United States Patent [19]

Robinson et al.

[11] Patent Number: 5,242,384
[45] Date of Patent: Sep. 7, 1993

[54] BLOOD PUMPING AND PROCESSING SYSTEM

[75] Inventors: Thomas C. Robinson; Sotiris Kitrilakis, both of Berkeley, Calif.

[73] Assignee: Davol, Inc., Cranston, R.I.

[21] Appl. No.: 852,940

[22] Filed: Mar. 13, 1992

Related U.S. Application Data

[63] Continuation of Ser. No. 776,721, Mar. 4, 1991, abandoned, which is a continuation of Ser. No. 437,032, Nov. 13, 1989, abandoned.

[51] Int. Cl.⁵ .......................................... A61M 37/00
[52] U.S. Cl. .......................................... 604/4; 604/6; 604/269
[58] Field of Search .......................... 604/4–6, 604/30, 31, 51, 52, 82, 83, 118–120, 141–146, 151–153, 269

[56] References Cited

U.S. PATENT DOCUMENTS

| | | | |
|---|---|---|---|
| Re. 31,688 | 8/1984 | Popovich et al. | 604/6 |
| 2,689,565 | 9/1954 | Gobel. | |
| 3,489,145 | 1/1970 | Judson et al. . | |
| 3,572,979 | 3/1971 | Morton | 417/390 |
| 3,579,441 | 5/1971 | Brown . | |
| 3,655,123 | 4/1972 | Judson et al. | 233/21 |
| 3,791,767 | 2/1974 | Shill | 417/389 |
| 3,811,800 | 5/1974 | Shill | 417/317 |
| 3,890,969 | 6/1975 | Fischel . | |
| 3,974,825 | 8/1976 | Normann . | |
| 4,043,501 | 8/1977 | Larrabee et al. | 229/14 |
| 4,223,672 | 8/1980 | Terman et al. | 128/214 |
| 4,416,280 | 11/1983 | Carpenter et al. . | |
| 4,479,760 | 10/1984 | Bilstad et al. | 417/395 |
| 4,479,761 | 10/1984 | Bilstad et al. | 417/395 |
| 4,540,406 | 9/1985 | Miles | 604/269 |
| 4,552,552 | 11/1985 | Polaschegg et al. | 604/4 |
| 4,573,883 | 3/1986 | Noon et al. | 417/394 |
| 4,573,992 | 3/1986 | Marx | 604/408 |
| 4,619,639 | 10/1986 | Nose et al. | 604/6 |
| 4,631,050 | 12/1986 | Reed et al. | 604/4 |
| 4,634,430 | 1/1987 | Polaschegg . | |
| 4,648,866 | 3/1987 | Malbrancq et al. | 604/5 |
| 4,702,829 | 10/1987 | Polaschegg et al. | 210/195.2 |
| 4,707,335 | 11/1987 | Fentress et al. | 422/44 |
| 4,713,171 | 12/1987 | Polaschegg | 210/110 |
| 4,713,176 | 12/1987 | Schoendorfer et al. | 210/645 |

(List continued on next page.)

FOREIGN PATENT DOCUMENTS

| | | |
|---|---|---|
| 0094682 | 11/1983 | European Pat. Off. . |
| 0303765 | 2/1989 | European Pat. Off. . |
| 8500020 | 1/1983 | PCT Int'l Appl. . |

OTHER PUBLICATIONS

Stairmand et al., "Separation of Plasma from Whole Blood by Membrane Filtration in Oscillatory Flows", Life Support Systems, No. 3, Jul.–Sep. 1986, pp. 193–204.

An Automatic Pneumatically Driven Autotransfusion System: A Evaluation in Dogs, Surgery, Aug. 3, 1985, Wabeke, M. D., et al.

(List continued on next page.)

Primary Examiner—John D. Yasko
Attorney, Agent, or Firm—Wolf, Greenfield & Sacks

[57] ABSTRACT

Blood is pumped by a pump, preferably a bi-concave diaphragm pump. When the blood pump is full of blood, this full condition is detected and a batch of blood is emptied completely from the pump for delivery to the patient. A second pump, also preferably a bi-concave diaphragm pump, pumps anti-coagulant into the blood as it is recovered. This second pump ejects its contents every time the blood pump ejects its contents. Particulates in the blood are removed by a filter and air is removed by a defoamer. Fluid and very small matter in the blood may be removed in a tangential flow separator. Blood flows through a narrow passage along one or more membranes, with fluid and small matter passing through the membrane(s). A washing fluid may be added to blood within this separator. A third pump, again preferably a bi-concave diaphragm pump, is used to add this washing fluid. The third pump is emptied whenever the blood pump empties, and thereafter refills with washing fluid.

80 Claims, 8 Drawing Sheets

U.S. PATENT DOCUMENTS

| | | | |
|---|---|---|---|
| 4,772,256 | 9/1988 | Lane et al. | 604/4 |
| 4,775,360 | 10/1988 | Lane et al. | 604/4 |
| 4,775,482 | 10/1988 | Thurman | 210/668 |
| 4,776,964 | 10/1988 | Schoendorfer et al. | |
| 4,828,543 | 5/1989 | Weiss et al. | 604/4 |
| 4,850,995 | 7/1989 | Tie et al. | 604/6 |
| 4,850,998 | 7/1989 | Schoendorfer | 604/6 X |
| 4,850,998 | 10/1989 | Schoendorfer | 604/28 |
| 4,871,462 | 10/1989 | Fischel et al. | |
| 4,895,558 | 1/1990 | Cham | 604/4 |
| 4,897,185 | 1/1990 | Schuyler et al. | 210/90 |
| 4,911,703 | 3/1990 | Lysaght et al. | 604/6 |
| 4,919,817 | 4/1990 | Schoendorfer et al. | |
| 4,923,439 | 5/1990 | Seidel et al. | 604/6 |
| 4,935,002 | 6/1990 | Gordon | 604/4 |
| 4,954,128 | 9/1990 | Ford | 604/5 |
| 4,964,847 | 10/1990 | Prince | 604/5 |
| 4,981,596 | 1/1991 | Shiino et al. | 210/650 |
| 5,004,548 | 4/1991 | Richalley et al. | 210/646 |
| 5,034,188 | 7/1991 | Nakanishi et al. | 422/46 |
| 5,098,372 | 3/1992 | Jonsson | 604/5 |

OTHER PUBLICATIONS

Computer Simulation of Cascade Filtration Procedures, Plasma Separation and Plasma Fractionation, Tretzel, et al, pp. 235-244.

Donor Plasmapheresis by the Membrane Method, Current Practice In Therapeutic Plasmapherosis, Tamaura, et al (1985).

Extracorporeal Immunoadsorption, Current Practice in Therapeutic Plasmapherosis, Yamazaki, et al (1985).

On-Line Plasma Reporcessing by Convective Electrophoresis, Plasma Separation and Plasma Fractionation, pp. 303-311, Pouratt, et al 1983.

Technical and Therapeutic Applications by Plasma Exchange, Apheresis: Development, Applications and Collections Procedures, pp. 123-145, Nielke, Jr., et al (1981).

"Microemboli-free Blood Detoxification Utilizing Plasma Filtration," Castino, F., Scheucher, K., Malchesky, P., Koshino, I., and Nose, Y., Trans. Amer. Soc. Artif. Int. Organs, vol. 22, pp. 637-645, 1976.

FIGURE I

BLOOD PUMPING AND PROCESSING SYSTEM

This application is a continuation of Ser. No. 776,721, filed Mar. 4, 1991, now abandoned, which is a continuation of Ser. No. 437,032, filed Nov. 13, 1989, now abandoned.

FIELD OF INVENTION

The invention relates to a pumping apparatus and method for use in the processing of blood. Blood can be filtered and undesirable substances removed, other substances can be added, or the blood can be otherwise treated and then administered to a patient, for example, during a surgical procedure.

BACKGROUND OF THE INVENTION

The pumping and processing of blood has been routinely performed with patients as a means of processing their own blood or blood taken from another person and administered to the patient. Blood processing can be performed to remove a variety of blood constituents for therapeutic purposes. Hemodialysis is a widely used processing methodology that removes metabolic waste products from the blood of patients suffering from inadequate kidney function. Blood flowing from the patient travels across membranes which remove these waste products. The processed blood is then returned to the patient. Plasmapheresis similarly processes blood using tangential flow membrane separation to remove blood plasma constituents, such as cholesterol, to treat a wide variety of disease states. Membrane pore sizes are selected to remove the unwanted plasma constituents in a tangential or cross-flow separator. Hemoconoentrators use membranes with very small pores or non-porous membranes which permit water diffusion, to remove water or fluid with electrolytes from blood that is too dilute. Blood may similarly be processed in a device which utilizes biochemical reactions to modify biological constituents present in blood as a treatment for certain diseases. For example, enzymes can be bonded to membrane surfaces or gel immobilized and blood components such bilirubin or phenols can be gluconized or sulfated by the in Vitro circulation of blood plasma across these bonded enzyme surfaces. Blood is routinely processed by the addition of an anticoagulant to prevent its clotting While it is outside the body.

Blood may be processed during surgery to permit blood flowing from a wound or incision to be reinfused into the patient. This is called intraoperative autotransfusion. Such processing may include anticoagulation and the removal of particles (debris from the wound site and clots) larger than red cells. This processing may include the removal of blood plasma and damaged blood tissue components (i.e., free plasma hemoglobin) and anticoagulant, with or without the addition of a saline washing fluid to aid in plasma removal and to replace some of the lost fluid.

Techniques and apparatus have been available for some time for washing blood cells prior to returning them to the patient. In such techniques a centrifuge is used for separating and washing the red cells in batches and they are resuspended in a balanced salt solution before infusion into the patient. This is a relatively slow process, the apparatus is complex and expensive and considerable expertise is needed to run the apparatus.

More recently, as set forth in U.S. Pat. No. 4,631,050, issued to Charles C. Reed and Denton A. Cooley on Dec. 23, 1986, an autotransfusion system is utilized wherein the centrifuge is replaced by an ultrafiltration module. The apparatus utilizes a receiving chamber having a semipermeable membrane at least partially bonded to its inside surface. The chamber is pressurized so as to provide a significant pressure differential across the membrane and fluid and small particles are forced out of the blood and through the membrane while the membrane holds up the red cells. Thereafter, washing solution is indebted into the receiving chamber to assist in plasma removal and the blood cells, along with some of the washing fluid, are swept out of the chamber and reinfused into the patient.

The system and method of U.S. Pat. No. 4,631,050 suffer from a number of problems. One of the problems is that a thick layer of red cells is formed and is retained above the ultrafiltration membrane. This requires that a relatively high pressure be provided across the membrane to achieve any practical plasma removal rate. This limits the speed of filtration. Also, the red cells held against the membrane can be damaged when subjected to the pressure differential whereby the proportion of undamaged red cells recovered and reinfused into the patient is limited. Further, the apparatus of U.S. Pat. No. 4,631,050 utilizes roller pumps which can themselves damage red cells thus still further reducing the proportion of red cells returnable to the patient. In addition, there is no means for mixing washing fluid and blood uniformly to obtain efficient washing. Also, washing fluid is added before any ultrafiltration which requires relatively large quantities of washing fluid for plasma removal. The apparatus of U.S. Pat. No. 4,631,050 only provides for batchwise addition of washing fluid rather than continuous addition of washing fluid whereby washing is not as efficient as would be desired.

In plasmapheresis membrane tangential flow separators have been utilized to remove plasma from blood as an alternative to centrifugation. U.S. Pat. No. Re. 31,688 reissued Sep. 25, 1984 to R. P. Popovioh, J. W. Monorief and G. D. Antwiler discloses one such process. Such is also reported, for example, by M. Tamura and M. Kasai in Current Practice in Therapeutic Plasmapheresis, pp 70–77, Edited by Y. Shiokawa and N. Inoue, Excerpta Medica, Amsterdam, 1985 as well as by Z. Yamazaki, et al, pp 78–85, same book. Such membrane tangential flow separators have not, however, been known to be useful or been used in autotransfusion wherein very different problems are encountered. In plasmapheresis one has a consistent supply of whole blood, for example, from a blood vessel, and the blood flows at a relatively constant rate. In autotransfusion the rate of blood flow varies from zero on up to many times that which occurs in plasmapheresis and can do this several times intermittently during a surgical procedure. Also, it is not whole blood which flows but rather a mixture of fluids which include traumatized blood, clots, debris, entrapped gases, and the like. Tangential flow separators are generally unable to handle such a mixture and would be damaged and/or clogged if one attempted to separate such a mixture using a plasmapheresis tangential separator apparatus.

The current systems for intraoperative autotransfusion, plasmapheresis, hemoconcentration, hemodialysis, and blood processing in general suffer from a number of problems. All are complex electromechanical systems which are expensive and require a trained operator as well as much time to set up and use. The systems are manual or semiautomatic but not automatic. They are not inherently safe but require sensors and safeguards and much attention to ensure safe operation. The processing of blood often occurs at rates lower than desired. The metering and mixing of anticoagulant with blood is often inadequate, leading to insufficient anticoagulation and clotting or excessive anticoagulation, higher cost for the anticoagulant, and the need to remove this excess (or all anticoagulant) before returning blood to the patient. Damage to retained blood constituents or excess removal of those which are desired to be retained often occurs with these systems. It is desired to retain close to 100% of the red cells and a significant proportion of platelets for return to the patient. Present systems retain substantially less than 100% of the red cells and a very low percentage of the original platelets.

The present invention is, in some of its embodiments, intended for use in all of the blood pumping and processing applications mentioned above, and in other embodiments, intended for use in autotransfusion, and is directed to overcoming one or more of the problems of existing devices as described herein.

DISCLOSURE OF INVENTION

In accordance with an embodiment of the invention particularly adapted for autotransfusion a blood pumping, filtering and separating apparatus is provided. A filter receives a mixture of blood cells, platelets, blood fluid and particulate matter and removes at least a portion of the particulate matter larger than blood cells. The filter has an outlet port from which the resulting filtered mixture exits. A main pump has a pumping chamber having a pump inlet port arranged to receive the filtered mixture and a pump outlet port from which the filtered mixture is pumped. Check valve means is located between the outlet port and the pump inlet port. It serves for preventing flow from the pumping chamber into the filter and for allowing flow from the filter outlet port to the pump inlet port when the filtered mixture is not being pumped out of the pump outlet port. A tangential flow separator has a narrow passage having a porous membrane having an infacing and an outfacing surface, and extending along the passage, the passage being no more than about 500 microns across. The passage extends from a separator inlet to a separator outlet. Delivery means serves for delivering the filtered mixture from the pumping chamber to the passage at a pressure in the passage sufficient to impel blood fluid through the porous membrane and at a flow rate through the passage sufficient to prevent the blood cells and platelets from blocking or passing through the porous membrane. Fluid removal means serves for removing blood fluid from the outfacing surface. A pressure adjacent the outfacing surface of the membrane is maintained less than the pressure in the passage.

In accordance with an additional embodiment of the invention useful in a number of blood processing operations a blood pumping and fluid introduction apparatus is set forth. The apparatus comprises a main pump having a pumping subchamber having a pump inlet port arranged to receive blood and a pump outlet port from which said blood is pumped, the main pump having a substantially bi-concave main pump chamber divided by a main pump diaphragm into the pumping subchamber and a pressurization subchamber. A blood delivery system is present for delivering blood to the pump inlet port. Valve means is present between the blood delivery system and the pump inlet port for (1) preventing flow from the pumping subchamber back into the blood delivery system and for (2) allowing flow from the blood delivery system to the pump inlet port when blood is not being pumped out of the pump outlet port. Means is present for determining when the main pump pumping subchamber is substantially full. Main pump pressurizing means is present for pressurizing the main pump pressurization subchamber, in response to the main pump pumping subchamber being substantially full, sufficiently to impel substantially all of the blood out of the pump outlet port. A fluid introduction pump is positioned to deliver a fluid to the blood. Means is present for respectively starting and stopping the fluid introduction pump in response respectively to starting and stopping of pumping of the main pump.

In accordance with another embodiment of the present invention useful in a number of blood processing operations a blood pumping and processing apparatus is disclosed. The apparatus comprises a rigid main pump housing having an internal wall structure defining a bi-concave chamber. A main pump diaphragm is sealed at its periphery to the internal wall structure, the main pump diaphragm dividing the chamber into a pressurization subchamber and a stroking subchamber. The diaphragm is of a shape and size sufficient to fit substantially matingly against the internal wall structure defining either of said subchambers and is formulated of a material which is sufficiently flexible to allow it to fit substantially matingly against the internal wall structure defining each of the subchambers whereby by diaphragm motion and flexing each of said subchambers can vary in size from substantially zero volume to substantially the volume of said chamber. Inlet valve means is present for delivering blood to said stroking chamber and for preventing backflow. Outlet valve means is present for permitting blood to leave the stroking chamber and for preventing backflow. Means is present for controlling the rate of flow of blood out of the stroking chamber. Means is present for pressurizing the pressurization subchamber at a controlled rate sufficiently to motivate the diaphragm to substantially matingly fit against the internal wall structure defining the stroking chamber to expel substantially all blood in the stroking subchamber through the outlet valve means. Means is present for depressurizing the pressurization subchamber at a controlled rate sufficiently to motivate said diaphragm to substantially matingly fit against the internal wall structure defining the pressurization subchamber. Means is present for sensing when the stroking subchamber is substantially full and for activating the pressurizing means when the stroking subchamber is substantially full. Means is also present for processing blood flowing to or from the main pump.

In accordance with yet another embodiment of the present invention particularly adapted for autotransfusion a method is set forth of separating blood cells from blood plasma. A mixture of healthy blood cells, platelets, plasma, particulate matter and entrapped gases is filtered and defoamed to remove at least a portion of the particulate matter and at least a portion of the entrapped gases to form a defoamed and filtered mixture. The defoamed and filtered mixture is pumped through a tangential flow separator having a narrow passage having a porous membrane having an infacing surface and an outfacing surface and extending along the passage, the passage being no more than about 500 microns across. The passage extends from a separator inlet to a separator outlet. The filtered mixture from the pumping chamber is delivered to the passage at a pressure in the passage sufficient to impel plasma through the porous membrane and at a flow rate through the passage sufficient to prevent the blood cells and platelets from blocking or passing through the porous membrane. Plasma is removed from the outfacing surface of the membrane by maintaining a pressure adjacent the outfacing surface of the membrane as less than that in the passage.

The apparatus and method in accordance with certain embodiments of the present invention operate with a relatively low pressure differential across the membrane in the tangential flow separator, when such is present. The red cells and platelets are not held by the membrane but, instead, are constantly stirred up and in flowing along the membrane. This hydrodynamically prevents deposition of cells on to the membrane and concurrent blocking of the pores of the membrane when the membrane pores are smaller than the cells and platelets and hydrodynamically prevents the cells from passing through the membrane when the membrane pores are larger than the cells and platelets. The velocity of the plasma plus red cells and platelets through the passage is kept high enough to maintain the required tangential flow yet low enough so that damage to the red cells and platelets is minimized. Washing fluid can be added whereby dilution aids in removal of blood substances which can pass through the membrane. The washing fluid can be added during the entire time that the plasma and red cells flow through the passage thus leading to highly efficient processing.

The pump of the present invention provides pumping at a controllable rate with minimal damage to the blood cells and platelets and is useful in a number of blood processing applications. Anti-coagulant fluid and/or other fluids, e.g., washing fluid, a diluent such as normal saline, a therapeutic agent, a diagnostic substance such as a contrast medium, etc., can be added in direct proportion to the amount of blood being pumped to fix the volumetric ratios of blood, anti-coagulant fluid, washing fluid, etc. Or, the blood can be otherwise processed, for example, by hemodialysis, hemoconcentration, plasmapheresis, biochemical reactions, or other methods. Embodiments of the system can be used in blood removal and storage, intraoperative autotransfusion, or post surgical chest drainage with blood return.

BRIEF DESCRIPTION OF DRAWINGS

The invention will be better understood by reference to the figures of the drawing wherein like numbers denote like parts throughout and wherein.

BEST MODE FOR CARRYING OUT INVENTION

Figure 1:
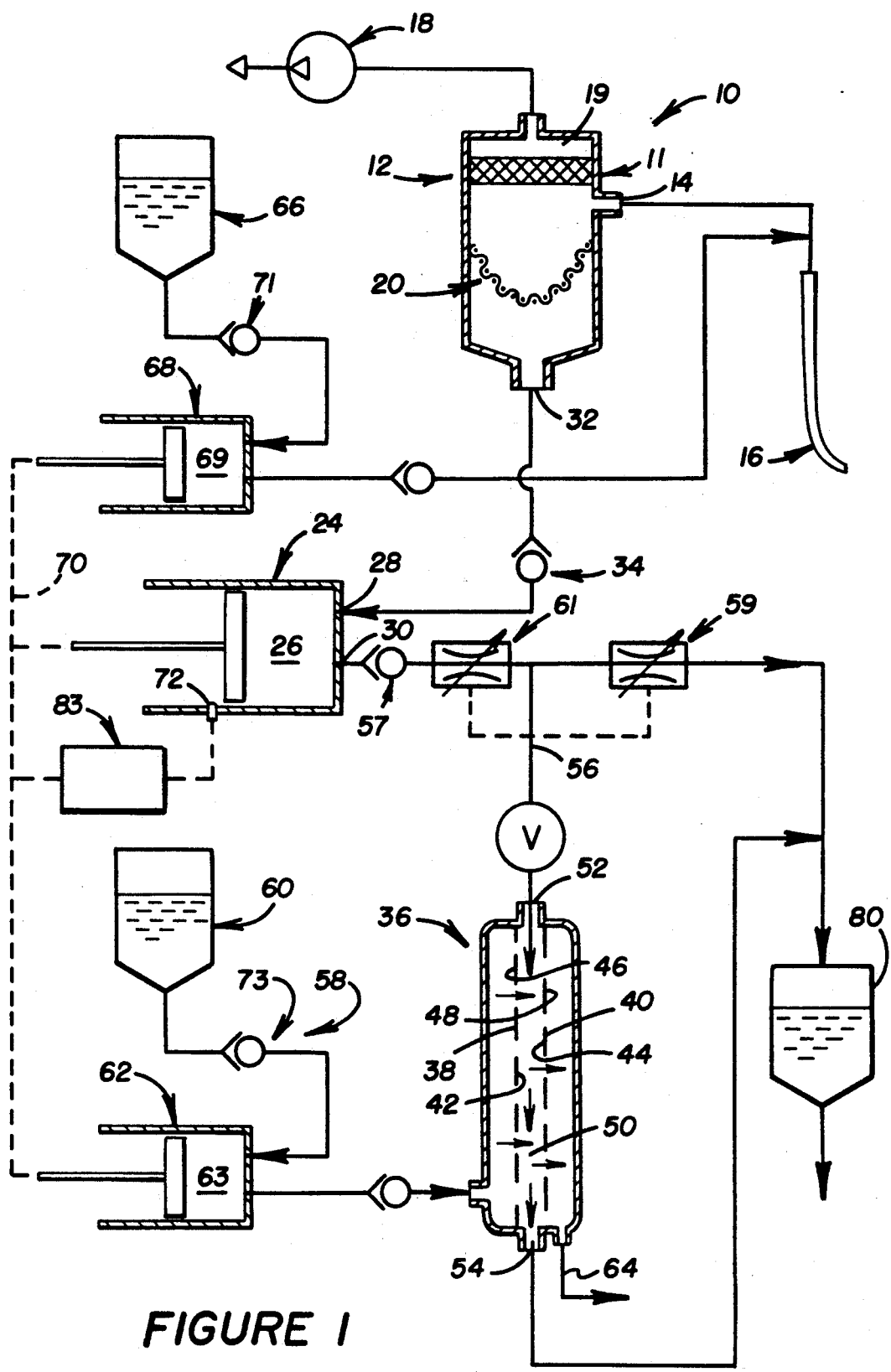
FIG. 1 illustrates, schematically, a method and apparatus in accordance with an embodiment of the present invention.

FIG. 1 illustrates, schematically, a blood filtering and tangential flow blood cell and platelet washing apparatus 10 in accordance with an embodiment of the present invention. The apparatus 10 includes a defoaming and coarse filtering unit which includes a defoamer 12 having an inlet port 14 which serves for receiving a recovered mixture of healthy blood cells, platelets, fluid (including plasma), particulate matter and entrapped gases. The defoamer 12 is capable of removing at least a portion of the entrapped gases from the mixture to form a defoamed mixture. The term "entrapped gases" as used herein includes gases in bubbles and foam plus large slugs of air which may be picked up by a suction wand 16 when it is not drawing blood.

The recovered mixture of healthy blood cells, platelets, fluid, particulate matter and entrapped gases is generally picked up by the suction wand 16 through application of a vacuum from a vacuum source 18 to the defoamer 12 at a position above the inlet port 14. The vacuum source 18 communicates above the liquid level, namely with a non-liquid filled chamber 19, in the defoamer 12. Thus, the vacuum source 18 does not remove significant amounts of blood cells or fluid. The vacuum source 18 does remove at least a portion, generally most, of the entrapped gases.

A filter 20 which generally provides rough filtering to remove clots and other relatively large particles, in the embodiment illustrated a part of the unit 11, serves for removing at least a portion (the larger particle portion) of the particulate matter from the recovered mixture during and following the defoaming by the defoamer 12 to form a filtered mixture. It is also contemplated that the defoaming can follow the filtering or that the filtering can follow blood pumping. Indeed, two filters can be used, one before and one following blood pumping.

In accordance with the embodiment illustrated in FIG. 1 the filter 20 and the defoamer 12 are all part of the single defoaming and filtering unit 11 although separate units may be used instead. In operation the recovered mixture of healthy blood cells, platelets, fluid, particulate matter and entrapped gases enters the defoaming and filtering unit 11 via the inlet port 14 and the entrapped gases are pumped away from the chamber 19 by the vacuum source 18 while the healthy blood cells, platelets, fluid and particulate matter reach the filter 20. At least a portion of the particulate matter (particles larger than red blood cells) is held by the filter 20 while the healthy blood cells, platelets, and fluid, and generally a portion (the debris smaller than red blood cells and smaller than platelets) of the particulate matter, pass through the filter 20 for treatment as is described below.

A main pump 24 has a stroking or pumping chamber 26 having a pump inlet port 28. While FIG. 1 shows piston pumps and while such are usable in some embodiments of the invention, diaphragm pumps are preferred to minimize cell and platelet damage and to permit the diaphragm pumps to be part of an inexpensive disposable assembly. The pump inlet port 28 is arranged to receive the defoamed and filtered mixture. A pump outlet port 30 communicates with the pumping chamber 26 and serves as an outlet for the defoamed and filtered mixture. Between an outlet port 32 of the defoaming and filtering unit 11 and the pump inlet port 28, a valve 34, such as the float check valve shown, is located which serves as means for preventing flow from the pumping chamber 26 back towards the defoaming and filtering unit 11 and for allowing flow from the defoaming and filtering unit outlet port 32 to the pump inlet port 28 when the defoamed and filtered mixture is not being pumped out of the pump outlet port 30. In practice, the pumping chamber 26 fills with a batch of blood and other fluids picked up by the wand 16, that batch is pumped out of the pumping chamber 26, then another batch is collected in the pumping chamber 26, etc. Since bleeding rates vary greatly during an operation there are often times when the pump 24 is idle, i.e., receiving little or no blood and pumping only occasionally.

A tangential flow separator 36 forms an important part of one embodiment of the invention. The tangential flow separator 36 has first and second spaced apart membranes 38 and 40 having respective infacing surfaces 42 and 44 and respective outfacing surfaces 46 and 48. Both membranes are porous to aqueous liquids and the second membrane 40 will allow fluid and particulate matter smaller than red cells and than platelets (platelets are slightly smaller than red cells) to pass through it. Preferably the pores of the second membrane 40 will be too small to permit passage of red cells or platelets since if flow is interrupted some of the red cells and platelets can then pass through the pores leading to a loss of such cells and platelets. However, the pores can be large enough to allow red cells and platelets to pass through the second membrane 40 since during flow the cells and platelets are hydrodynamically prevented from passing through the pores. The infacing surfaces 42 and 44 define a narrow flow through passage 50 therebetween of no more than about 100 red cell diameters (no more than about 500 microns), preferably of no more than about 300 microns, across, the passage 50 extending from a separator inlet 52 to a separator outlet 54. A number of such passages 50 can be used in parallel or in series in the tangential flow separator 36. The passages 50 can be in a bundle of, for example, hollow fibers having porous membrane walls or can be a plurality of generally flat passages 50 made from membrane sheets.

Fluid from the pumping chamber 26 is delivered via a conduit 56 and past a valve 57 such as the check valve shown, which together serve as delivery means, to the passage 50, and more particularly to the separator inlet 52, generally at substantially the pumping pressure, P. A bypass valve 59 allows return of the defoamed and filtered blood to a blood storage bag 80 and subsequently to the patient without use of the tangential flow separator 36 or washing action. This can be used when the recovered blood is relatively clean and undamaged. Also, the bypass valve 59 can be automatically opened if blood flow rate from the main pump 24 exceeds the blood flow rate capability of the separator 36, for example, if bleeding during an operation is excessive for a time. This condition can be detected by a flow meter 61 and the valve 59 can be a solenoid valve actuated by the flow meter. The bypass valve 59 and associated tubing may also be used with other embodiments of the invention.

FIG. 1 also illustrates washing fluid delivering means 58 in accordance with an embodiment of the invention. A washing fluid supply 60 and a washing fluid pump 62, serve for delivering washing fluid at a pressure, $P_1$, against the outfacing surface 46 of the first membrane 38, $P_1$ being sufficiently greater than P, whereby the washing fluid flows through the first membrane 38 and into the passage 50. The washing fluid is generally flowed in through the first membrane 38 along the length of the passage 50 to provide continuous and distributed diluting and washing action.

Fluid removing means, in the embodiment illustrated a conduit 64 from which waste fluid is removed, serves for removing a mixture of blood fluid, very small matter (smaller than red cells and platelets) and washing fluid from the outfacing surface 48 of the second membrane 40. A pressure, $P_2$, adjacent the outfacing surface 48 of the second membrane 40 is maintained at less than P. If desired a pump 65, of the nature illustrated in FIG. 7, may be included in the conduit 64 to further control the plasma flow rate and the pressure differential $P-P_2$.

The pressure differentials $P_1-P$ and $P-P_2$ are maintained such that the washing fluid flows through the first membrane 38 and into the central narrow flow-through passage 50 at a desired rate. The membrane 38 generally uniformly distributes the washing fluid into the flowing blood over the entire length of the infacing surface 42 of the first membrane 38. Blood fluid along with washing fluid are likewise generally removed over the entire length of the infacing surface 44 of the second membrane 40 which defines the central narrow flow-through passage 50. Blood and washing fluid are thoroughly mixed within the passage 50 due to the relatively high blood velocity. The advantages of this method for washing fluid addition, compared to adding washing fluid before filtration, are considerable. First, the washing fluid continuously dilutes the blood when it is flowing through the passage 50 so that blood viscosity is reduced in all parts of the passage 50 and consequently fluid removal rates are higher. Second, sequential or serial dilution accompanying plasma removal results in decreased flow rate and consumption of washing fluid and more effective removal of unhand constituents (e.g., particulate matter smaller than red cells and platelets, as well as anticoagulant).

The blood velocity through the passage 50 must be in a range such that a flow regime is realized in which a fluid boundary layer is hydrodynamically established immediately adjacent to the second membrane 40 which is such that blood cells and platelets are hydrodynamically prevented from layering upon and blocking the porous membrane 40. Indeed, it is possible to use a porous second membrane 40 with pores large enough for blood cells and/or platelets to pass through with the blood cells and/or platelets being prevented hydrodynamically from doing so due to shear forces adjacent the membrane 40. Basically, the fluid velocity, V, must be maintained of the proper magnitude, as is known for plasmapheresis, to keep cells from either blocking or passing through the pores of the second membrane 40. The deposition of cells and platelets onto the second membrane 40 or the passage of cells and platelets therethrough is thereby hydrodynamically prevented in the manner known for plasmapheresis. This increases plasma flow through the membrane 40 and prevents or minimizes cell and platelet damage. The blood fluid velocity should not be too high or significant red cell and platelet damage can occur. Generally the velocity, V, of the blood through the passage 50 should be in the range from about 50 to about 1000 cm/min, more preferably from about 200 to about 500 cm/min. The broader range corresponds to shear rates from about 1000 to about 2500 sec$^{-1}$ based upon channels of from about 100 microns to about 250 microns across.

Figure 6:
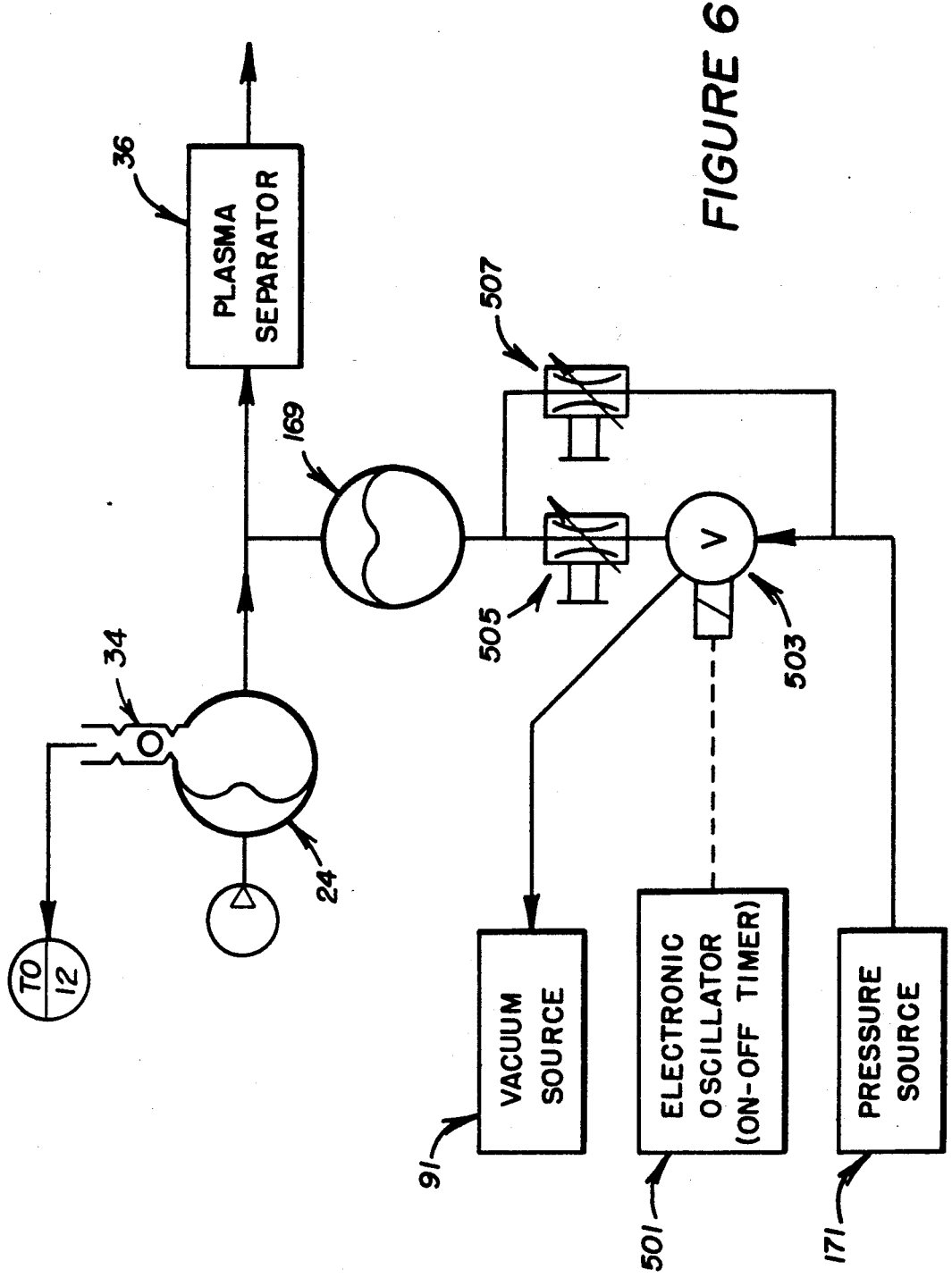
FIG. 6 illustrates, schematically, still another alternate embodiment of a portion of an apparatus in accordance with the present invention.

The complete mixing of red cells, white cells, and platelets with fluid within the separator blood flow-through passage 50 increases the rate at which fluid can be removed from the porous membrane 40 by decreasing the usual concentration of these cells near the membrane 40. Such mixing is achieved in part by high blood velocities. The use of oscillations in pressure or flow within the blood flow-through passage 50, which can be induced, for example, by providing oscillations adjacent the outfacing surface 48 of the membrane 40 (on the plasma side), provide additional mixing. Such oscillations can alternatively be superimposed on the actuating gas of the blood pump 24, the wash fluid pump 62, blood accumulator 169, wash fluid accumulator 175 or waste fluid accumulator (not shown). This may be accomplished by, for instance, use of a cycled solenoid valve 503 (FIG. 6) which provides a specific frequency and pressure, flow, or volume amplitude for optimal mixing. Flow control valves or orifices 505,507 are adjusted or selected for appropriate magnitude of oscillation. These oscillations may be used to change the pressure differential from blood to plasma sufficiently to periodically back flush the membrane 40. They may also be used to move the membrane 40 itself sufficiently to cause blood mixing.

The pressure, $P_2$, is generally near atmospheric pressure since conduit 64 usually simply leads to waste fluid storage (not shown). However, reduced pressure can be utilized or even pressures above atmospheric. All that is important is that $P_1$ be greater than P which in turn must be greater than $P_2$. Generally the pressure, P, will exceed the pressure $P_2$ by about 25 mm Hg to about 150 mm Hg, more preferably from about 50 mm Hg to about 100 mm Hg. Generally the pressure differential $P_1 - P$ will fall within a range from about 1 mm Hg to about 50 mm Hg, more preferably from about 5 mm Hg to about 25 mm Hg. The relatively low pressure differential, $P - P_2$, can be utilized because of the fact that the cells and platelets are not held by and do not block the second membrane 40.

Figure 7:
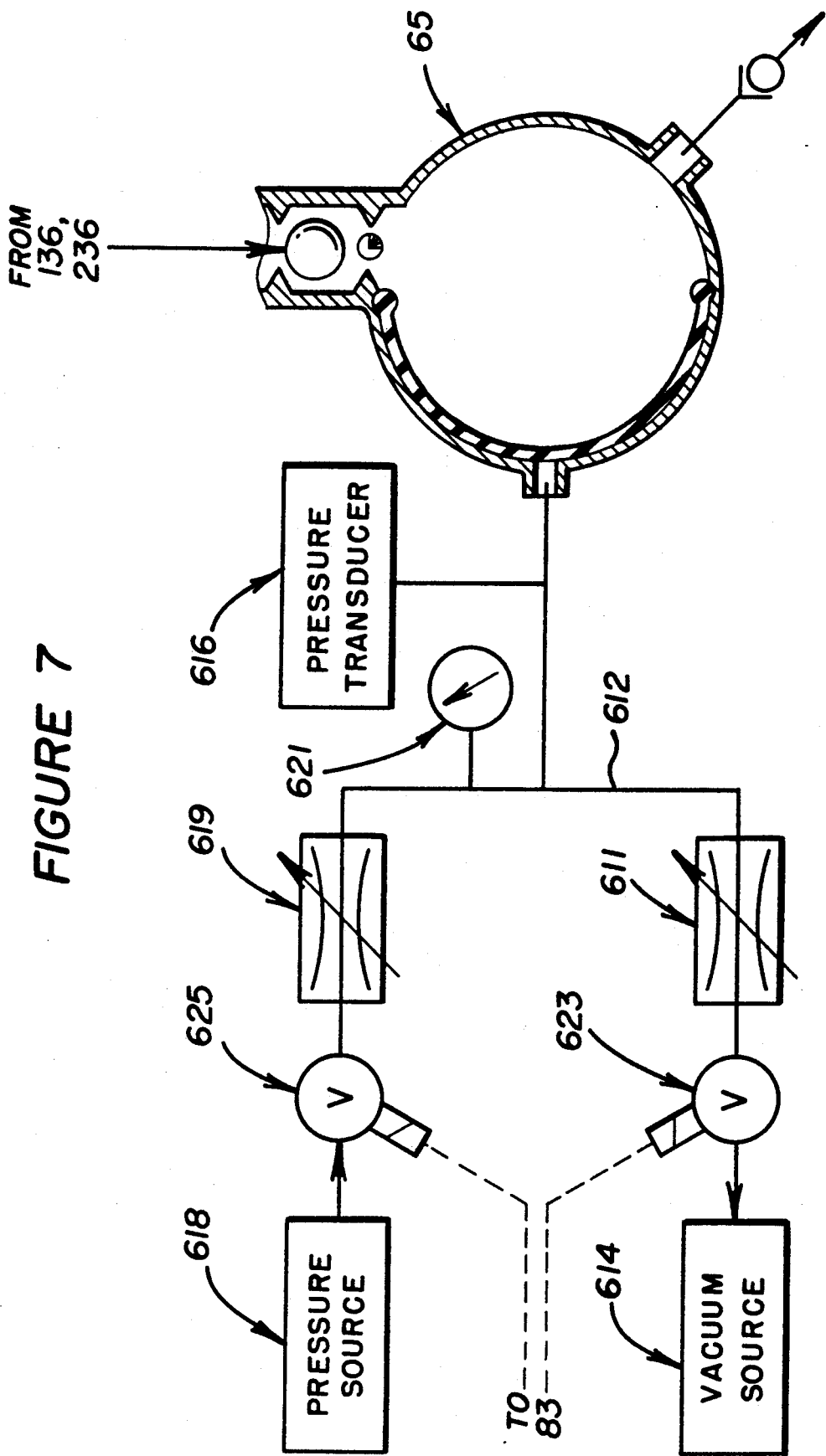
FIG. 7 illustrates, schematically, another alternate embodiment yet of a portion of an apparatus in accordance with the present invention.

As illustrated in FIG. 7, a waste fluid pump 65 may be used to control the rate of waste fluid removal and thereby the pressure, $P_2$. FIG. 7 illustrates a variation on the embodiment of FIG. 2 wherein the waste fluid pump 65 receives the outflow (controlled by the suction developed by the pump 65) of waste fluid from the separators 136 and 236 and delivers the waste fluid for disposal. However, the waste fluid pump 65 can also be used with other embodiments of the invention, for example, when there is only a single separator 36. The waste fluid pump 65 can suitably be a diaphragm pump of the same nature as is the main pump 124 of FIGS. 2 and 3. However, the waste fluid pump 65 operates out of phase with the main pump 124 in that when the main pump 124 is pumping fluid the waste fluid pump 65 is filling with fluid and when the main pump 124 is filling with fluid the waste fluid pump 65 is pumping the waste fluid past an exit line check valve. The waste fluid pump 65 can operate at a fixed flow rate, if desired. Such can be accomplished by adding a flow meter 621, a pressure sensor 616, a pressure source 618, a vacuum source 614, appropriate orifices 611 and 619, solenoid valves 623 and 625 and a controller and timer 83 of the nature of that shown in FIG. 3 to control the vacuum in a conduit 612 leading to the pressurization side of the waste fluid pump 65.

Figure 8:
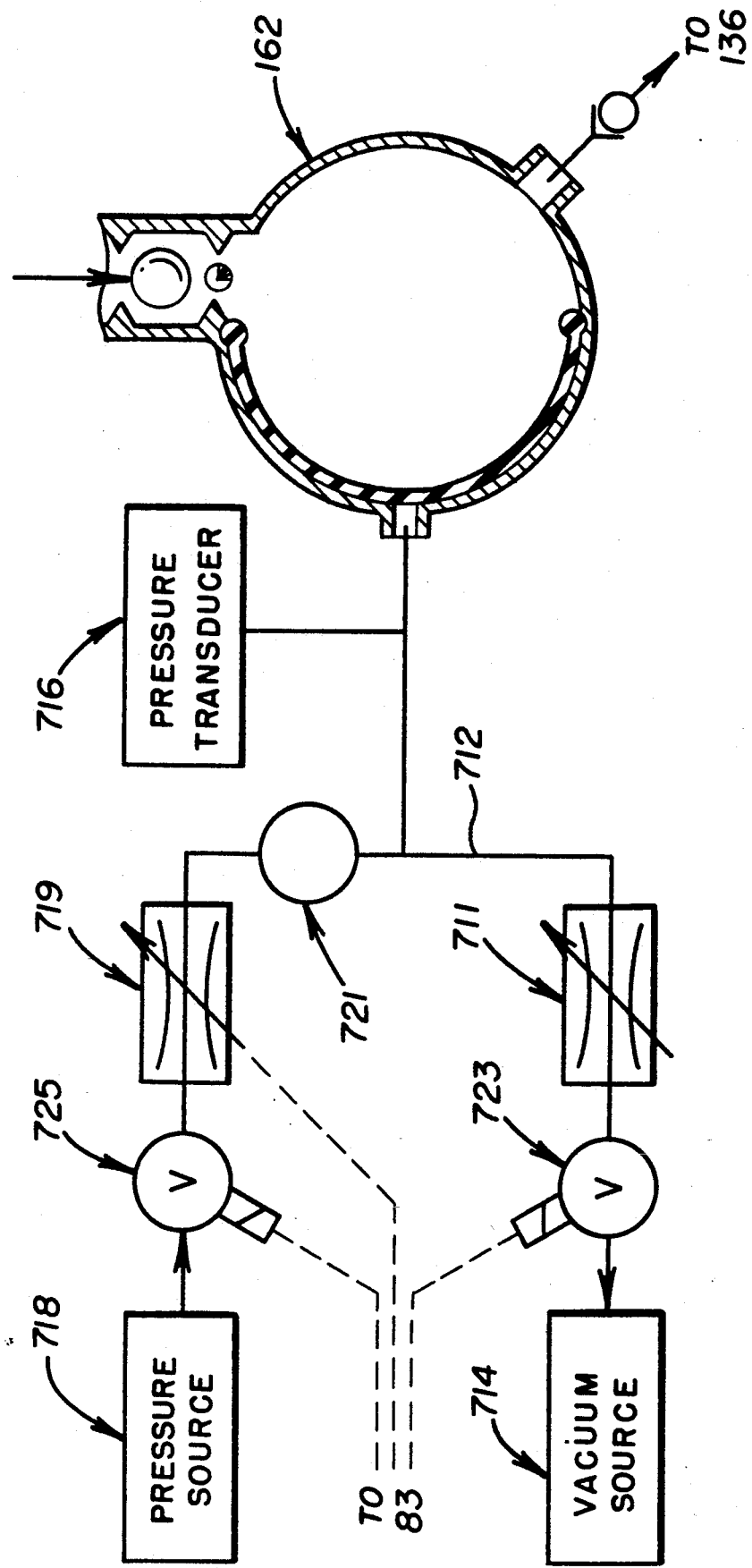
FIG. 8 illustrates, schematically, another alternate embodiment still of a portion of an apparatus in accordance with the present invention.

FIG. 8 (see in conjunction with FIG. 2) illustrates apparatus which can be used to control operation of the washing fluid pump 162. When the illustrated control scheme is used in conjunction with the apparatus shown in FIG. 7 for controlling operation of the waste fluid pump 65 the pumping volumes of the two pumps 162 and 65 can be coordinatedly selected to provide a given percent output hematocrit (usually in the range of 40%-60%) from the separators 136, 236 when the input hematocrit to the main pump 124 is a selected value (for example, in the range of 5%-40%) which is less than the given percent. The necessary control of the washing fluid pump 162 can be accomplished by adding a flow meter 721, a pressure sensor 716, a pressure source 718, a vacuum source 714, appropriate orifices 711 and 719, solenoid valves 723 and 725 and the controller and timer 83 to control pressure in a conduit 712 leading to the pressurization side of the washing fluid pump 162. The controller and timer 83 can suitably control the size of the orifice 719. In one embodiment the volume pumped, per stroke, by the waste pump 65 can be a fixed volume and the volume pumped, per stroke, by the washing fluid pump 162 can be varied to provide a desired output hematocrit.

In accordance with one embodiment of the present invention anti-coagulant delivery means are provided, in the embodiment illustrated in FIG. 1 an anti-coagulant supply 66, from which anti-coagulant is delivered in solution by an anti-coagulant pump 68 to the recovered mixture of healthy blood cells, fluid, particulate matter and entrapped gases between the suction wand 16 and the inlet port 14. The anti-coagulant introduction means is desirable because the recovered mixture would likely form blood clots within the blood pumping and processing system without the addition of the anti-coagulant. Furthermore, it is desirable that the anti-coagulant be added early so as to prevent coagulation during passage through the wand connecting tubing and the filter 20.

In accordance with an embodiment of the present invention operation of the washing fluid pump 62 and of the anti-coagulant pump 66 occurs along with pumping of the main pump 24 whereby each batch of blood pumped by the main pump 24 receives a proper amount of anti-coagulant and of washing fluid. This is indicated, schematically, by the dashed line 70 in FIG. 1. In FIG. 1 a sensor 72 senses the "full" position of the piston of the main pump 24. Generally, stroking of the main pump 24 is initiated when the pumping chamber 26 is completely full. At the same time, the pumping chambers, 69 of the anti-coagulant pump 68 and 63 of the washing fluid pump 62, are completely full having been filled from the respective supplies 66 and 60 via appropriate valves 71 and 73. Stroking of pumps 62 and 68 generally occurs simultaneously with the stroking of the main pump 24. While check valves are shown, other types of valves can be used with appropriate controls to open and close them.

It is desirable to have means for providing anti-coagulant flow when the amount of blood being aspirated by the wound 16 is small. In such an instance the main pump 24 is not stroking very often and insufficient anti-coagulant may be provided to the aspirated blood to prevent clotting in the coarse filtering unit 11. This can be accomplished by an electronic controller and timer 83 which has the capability to stroke the anticoagulant pump 68 independently of stroking of the main pump 24 and at a selected rate. Generally, independent stroking of the anti-coagulant pump 68 will occur only when the main pump 24 has not stroked after a selected time. The electronic controller and timer 83 can advantageously be used to control and time pumping of the main pump 124, the wash fluid pump 62 and the waste fluid pump 63.

In accordance with a preferred embodiment of the present invention (as illustrated, for example, in FIGS. 2 and 3) the main pump 124 is in the nature of a diaphragm pump. This minimizes cell and platelet damage during pumping as compared to roller pumps and piston pumps. The diaphragm pump 124 includes a rigid housing 100 defining a bi-concave chamber 102 which is divided by the diaphragm 74 into a stroking or blood pumping subchamber 26 and a pressurization subchamber 104. When the pumping subchamber 26 is full this fact is detected, for example, by a pressure measuring sensor 172 (see FIG. 3) which measures the pressure level in pressurization subchamber 104 as air is flowed in at a constant flow rate from pressurized gas source 204 (e.g., an air pump or cylinder). If the pressure increases above a threshold level in a selected interval of time, this indicates that the pumping subchamber 26 is full and pressurization is continued for a time period sufficient to pump all of the blood out of the pumping subchamber 26. If the pressure in pressurization subchamber 104 does not reach the threshold level, pressurization is discontinued at the end of the selected interval of time. After a time delay this procedure is repeated until the threshold level is reached.

Note that the threshold level is not reached when the pumping subchamber 26 is not full since the pumping subchamber 26 is then in communication, via the open float valve 34, the float 35 of which is below its seat 37, with a partial vacuum. When the pumping subchamber 26 is full of liquid the float 35 floats upwardly against its seat 37 and is accordingly closed. With the valve 34 closed the pressure in the pressurization subchamber 104 rises to above the threshold value to the pressure, P, entering the plasma separator 36. Then a fluid, for example air, is pumped into the pressurization subchamber 104 for a time period sufficient to empty pumping subchamber 26. The diaphragm 74 is then forced rightwardly in FIG. 2 until it generally matches the shape of the wall of the bi-concave chamber 102. At that time stroking of the main pump 124 is complete.

At the end of the pumping time period the defoamed and filtered mixture from the defoaming and filtering unit 11 can again flow past the ball check valve 34 and begin refilling the pumping chamber 26. The float 35 of the float valve 34 generally has a specific gravity of 0.8 to 1.0. This assures that when the pumping subchamber 26 is full the float 35 will float on top of the fluid and the float valve 34 will be closed. It also assures that any air and foam will not be dense enough to close the float valve 34 whereby the air and foam will be expelled upwards from and out of the pumping subchamber 26.

As has previously been stated the operation of main pump 124 can serve to trigger operation of the washing fluid pump 162 and of the anti-coagulant pump 168 for the same pumping time period (for one ejection stroke). Thus, when pressure is introduced into the pressurization subchamber 104 of the main pump 124, a like action takes place in similar diaphragm pumps 162 and 168. Control of activation of the various pumps 124, 162 and 168 can be via use of a conventional electronic controller/timer 83 which, on receiving a proper signal from the sensor 172, as indicated schematically by dashed line 85, opens the solenoid valve 87 while keeping the solenoid valve 89 closed. The solenoid valve 87 connects to a gas pressure source 204 while the solenoid valve 89 connects to a vacuum source 91. With the valve 87 closed the valve 89 can be opened to evacuate the pressurization subchamber 104 and draw the diaphragm 74 leftwardly in FIGS. 2 and 3. The various valves 99 illustrated are triggered or automatically opened check valves, which open in proper sequence with the pumps. Such valves may be float valves, mechanical check valves, solenoid valves, or electromechanical tubing pinch valves.

Flow control means 202, such as a flow control valve or fixed orifice, can advantageously be included to adjust or control the air flow rate into the pressurization subchamber 104. This assures that the pressure sensed by the pressure sensor 172 is determined by the pressure in the pressurization subchamber 104 rather than by the pressure of the gas pressure source 204. The flow control means 202 also partially controls the rate of flow of blood out of the pumping subchamber 26.

Figure 3:
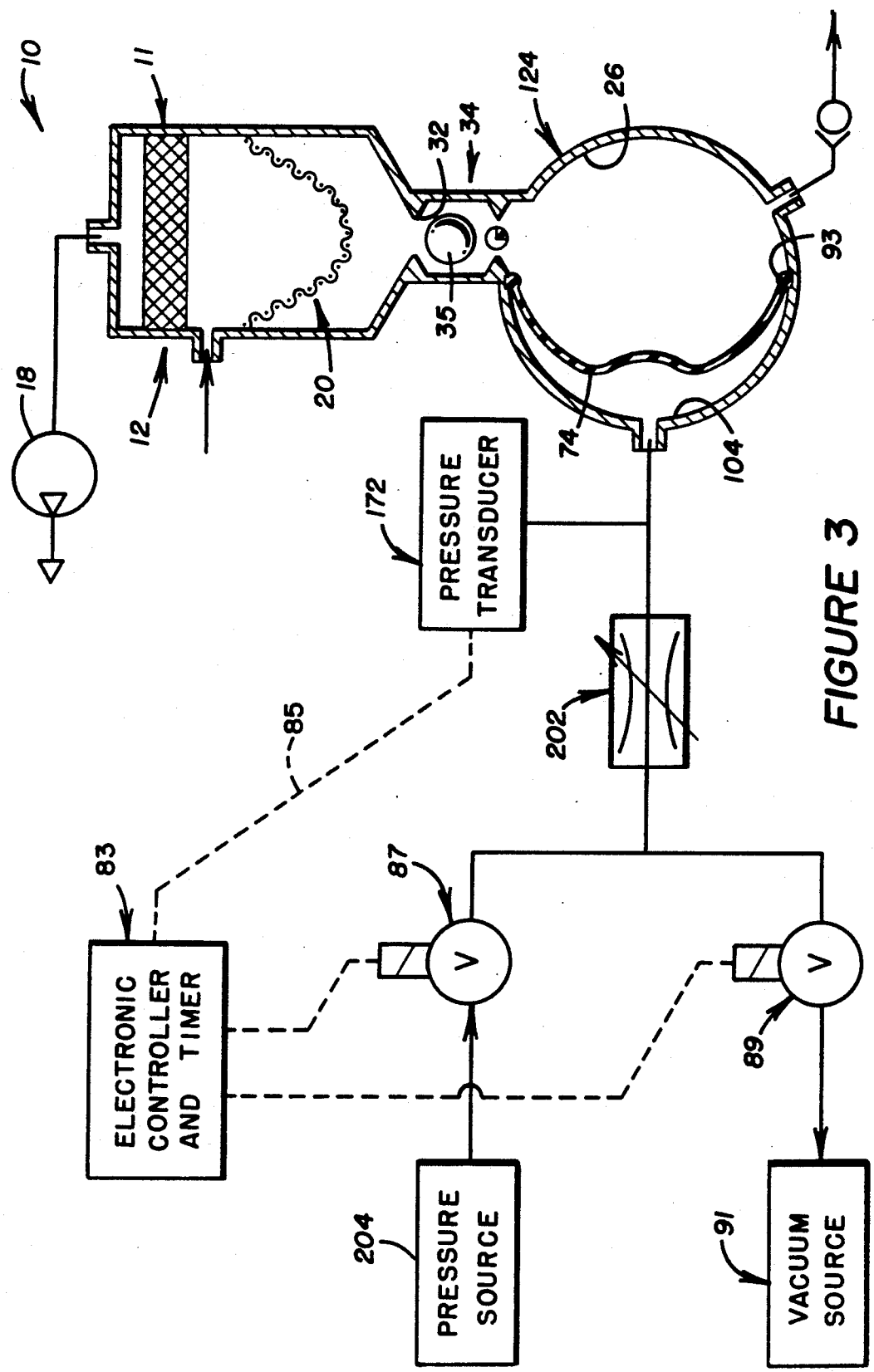
FIG. 3 illustrates, schematically, an embodiment of a portion of an apparatus in accordance with the present invention.

Referring to FIGS. 3 and 7, the electronic controller and timer 83 can provide electronic timing functions which turn the solenoid valves 87, 89, 623 and 625 ON and OFF. When the main pump 124 (of FIG. 3) is full of blood, the electronic controller and timer 83 can turn the solenoid valve 87 on and apply air pressure to the main pump 124. This begins ejection of blood. The source air pressure can be made relatively high (5 to 15 psig) and the flow controlling orifice 202 relatively small so that the pressure drop due to air flow across the orifice 202 is appreciably larger than the pressure drop due to blood flow through the main pump outflow check valve, blood flow through the separators 136, 236 and the blood bag height.

The total blood flow pressure drop typically ranges from about 0.5 psi to 3 psi, depending on the viscosity of the blood which varies with blood hematocrit. Inlet blood hematocrit is nominally anywhere within the range of 5–40% (volume percent of red cells in total fluid picked up). With the air flow pressure drop predominating, the time for ejection of all blood from the main pump 24 varies little with blood hematocrit, which is the objective. This time is main pump (stroke) volume divided by air flow rate. The change in blood volume is equal to the change in air volume. The electronic termination of ejection (pumping) time period and initiation of the blood filling time period is set slightly longer in time than that calculated to provide emptying in order to ensure complete ejection by main pump 24. The desired condition of constant flow through the plasma separators 136, 236 is approximated by having a long ejection time and a short fill time. For example, the actual ejection time may be about 16 seconds with a timed ejection of 17 seconds and a fill time of 3 seconds for a total cycle time of 20 seconds. Then, actual ejection is 80% of the total (cycle) time, or about as close to 100% as is feasible with this scheme of operation, and close enough for efficient use of the plasma separators 136, 236. The electronic controller and timer 83 sets the fill time sufficiently long (slightly longer than the actual time to fill) to ensure that complete filling will always occur. Actual fill time is controlled by the fill vacuum level and the fill needle valve or orifice.

The main pump 124 senses filling by initiating pressurization for ejection. The electronic controller and timer 83 looks at the rise in pressure in the air drive line to the main pump 124. This air pressure is virtually identical to the blood pressure because the flexible diaphragm 74 (when not supported by its housing when the main pump 124 is full or empty) has no pressure drop across it. If the main pump 124 is not full of blood, the float valve 34 will not close and the pressure will not rise above the reservoir vacuum level when measured a selected time, e.g., one second, after ejection pressurization begins. When ejection pressurization is terminated, a time delay of, e.g., two seconds, for filling occurs, and ejection pressurization begins again. When the main pump 124 is full of blood, the initiation of ejection closes the float valve and the air actuation pressure rises above an "ejection threshold" pressure (about +10 mmHg). The electronic controller and timer 83 does not terminate ejection when this "threshold" pressure is exceeded but continues it for a timed interval (i.e., a total of 17 seconds).

The actuation air pressure rises when main pump ejection is complete and the diaphragm is against the rigid pump housing. A "maximum pressure threshold" is set (perhaps 4 psi) at which ejection is immediately terminated and filling begins. However, a new ejection cycle will not begin until the complete cycle time (i.e., 20 seconds) has elapsed.

This maximum pressure termination of ejection prevents the main pump 124 from being exposed to high pressures and indicates to the actuator logic that complete blood ejection has occurred. If the timed end of ejection occurs without a maximum pressure threshold signal or termination, then it indicates that complete ejection has not occurred and a warning (of improper operation) may be provided to the user. It is advantageous to actuate the blood pump so that it always fills and empties completely.

The wash pump 62 is operated the same as the main pump 124 except that ejection of the wash pump 62 only continues when main pump 124 ejection continues, that is when the main pump 124 is full. Both pumps initiate ejection at the same time, test to see if the respective pump is full at the same time, and begin filling at the same time. Wash pump flow is variable as is described below. The wash pump 62 always fills completely, but does not empty completely.

The waste pump 65 is actuated at the same time as the main pump 124 but its filling duration is the main pump 124 ejection duration, and its ejection is the main pump 124 filling period. It has no test pulse to determine whether it is full or not. It is always operated to empty completely, but does not fill completely.

The basic control concept is to maintain the main pump 124 at an average flow rate, to maintain the waste pump 65 at an average flow rate and to vary the wash fluid pump 62 to achieve a flow rate which depends upon inlet blood hematocrit (which the electronic controller and timer 83 determines from the value of the actuation pressure of the main pump 124 as measured by the pressure transducer 172) and which results in an outlet hematocrit of 35%-65% (nominally 50%).

If, for example, the main pump 124 flow rate is an average value of 250 ml/min., the waste pump 65 flow rate is selected to give a 40% output hematocrit at a 5% inlet hematocrit with no wash fluid addition. This amounts to removing 92% of the plasma initially present without adding any wash fluid. Even a large error in wash fluid flow can be tolerated with the outlet blood hematocrit remaining in the desired 35% to 65% range.

Operating in the manner just described provides substantially constant outlet blood hematocrit (for example, in the range of 40%-60%) independent of the inlet hematocrit (for example, over the range of 5% to 40%) and source of blood (rapid bleeding and relatively undamaged; mixed with bone fragments and fat; or highly hemolyzed); addition of wash fluid to achieve plasma removal efficiencies of 90% or above; minimal surface area of the plasma separators 136,236; and maintenance of high blood quality (low hemolysis caused by pumps and separators; high platelet recovery).

Figure 2:
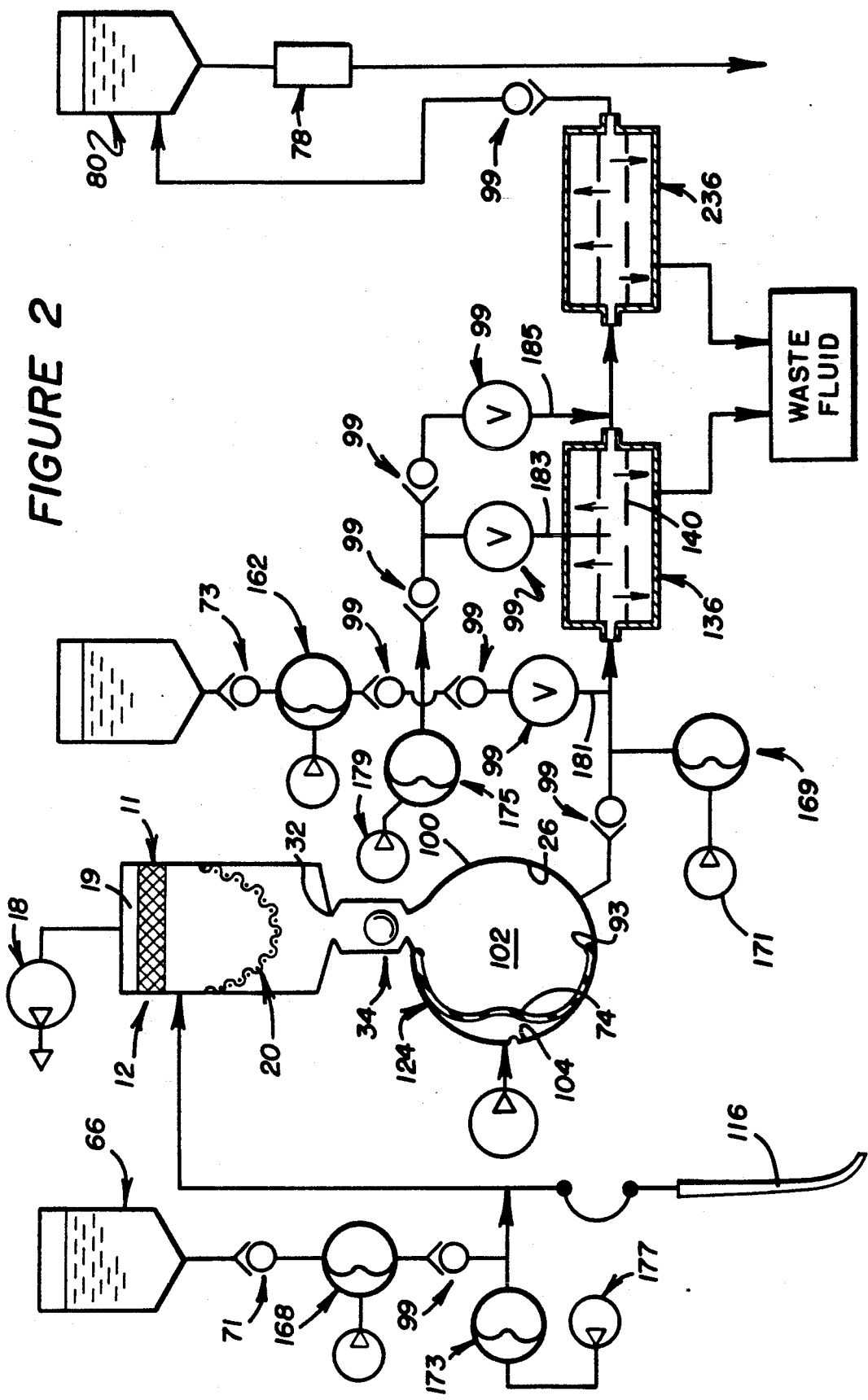
FIG. 2 illustrates, schematically, an embodiment of an apparatus in accordance with the present invention.

An accumulator 169, for example, a diaphragm accumulator as illustrated, may alternatively be used to store some of the blood exiting the main pump 124 so as to provide extra capacity to handle very high blood flow rates as can periodically occur during an operation. Also, between the pumping of each batch of blood by the main pump 124, that is, during those periods when the main pump 124 is not stroking, a relatively constant velocity flow can be maintained through the tangential separator 136. The accumulator 169 can be activated to propel blood through the tangential separator 136 by using pressurized gas from a gas pressure source 171, all as seen in FIG. 2 Similar accumulators 173 and 175 can be used, respectively, for the anti-coagulant and the washing fluid, using respectively, the gas pressure sources 177 and 179. Note that all gas pressure sources may connect to a single pump or source as may all vacuum sources.

The use of a diaphragm pump is particularly advantageous since such a pump does only minimal damage to any red cells and platelets being pumped by it and it is simple and inexpensive whereby it can be a disposable unit, e.g., made out of clear plastic. A disposable pump has the advantage that it does not contain viruses, bacteria, etc., from previous use. It is convenient to have both the washing fluid pump 162 and the anti-coagulant pump 168 also be diaphragm pumps since this makes coordinated operation very easy (using pneumatic actuation) along with metering of the amount of anti-coagulant being supplied to the blood being recovered from the wound, the amount of anti-coagulant being proportional to the amount of blood being pumped by the main pump 124. Similarly, the amount of washing fluid being pumped by the washing fluid pump 162 is proportional to the amount of fluid being pumped by the main pump 124 whereby a proper amount of washing fluid is supplied.

In accordance with an embodiment of the invention the diaphragm 74 of the main pump 124 (and generally the diaphragms of the washing fluid pump 162 and the anti-coagulant pump 168, when such are present) is sealed at its periphery 93 to the internal wall structure defining the chamber 102 and is of a shape and size sufficient to fit, without being stretched or expanded, substantially matingly against the internal wall structure defining, along with the appropriate side of the diaphragm 74, each of the subchambers 104 and 26. Thus, the diaphragm 74 does not need to elastomerically stretch and does not need to elastomerically expand on pressurization of the pressurization chamber 104, but does need to flex during its movement. The material of the diaphragm 74 can be flexible plastic (e.g., plasticized vinyl), elastomeric (e.g., polyurethane, silicone rubber) or whatever is desired, so long as it satisfies the above listed requirements and does not deleteriously affect the blood cells or platelets.

FIG. 2 also shows use of an optional microemboli filter 78 prior to reintroduction of the resuspended red blood cells into the patient. A flexible blood bag 80 will generally be present so as to provide a relatively constant pressure head and to control the rate of introduction of the resuspended blood cells and platelets into the patient.

FIG. 2 shows a tangential separator 136 for use in certain embodiments of the present invention and which differs from the tangential flow separator 36 of FIG. 1. The tangential flow separator 136 has a tubular membrane 140, which may be generally coaxial with the outer wall of the tangential flow separator 136, and through which plasma and particulate matter smaller than red cells and platelets will pass but through which red cells and platelets will not pass so long as flow is taking place. For example, the pores through the membrane 140 can be smaller than about 5 microns, the approximate diameter of a red cell (and of a platelet). Pores large enough to allow red cell and platelet passage can also be used with the flow rate preventing such passage.

In the embodiment of FIG. 2 washing fluid is not added through a membrane. Washing fluid may be, but is not necessarily, added upstream of (e.g., via line 181) and/or in the center of the tangential flow separator 136 (e.g., via line 183), all as illustrated. If it is not added the separator 136 merely removes plasma and small debris. This provides a concentrated red cell and platelet solution in which the cells and platelets can be washed more efficiently or can be returned to the patient without washing. If additional fluid is desired, washing fluid can be added downstream of separator 136 (e.g., via line 185).

If desired, an additional separator 236 can be downstream of the separator 136. The additional separator 236 can be of the nature of either the separator 36 or the separator 136 and may be accommodated in the same housing or structure as separator 136. The passage 150 can be a plurality of passages in, for example, a bundle of hollow cylindrical fibers having porous membrane walls or can be a plurality of flat passages made from membrane sheets. Appropriate valves 99, as illustrated in FIG. 2, can control and direct the needed flows.

The addition of wash fluid via line 183, or via line 185 if separator 236 is also used, has the major benefit of achieving dilution after fluid removal such that subsequent fluid removal eliminates more of the original fluid in the blood entering separator 136. This permits less washing fluid to be used for the same percent reduction in original blood fluid compared to the amount needed when introduced at the entrance to separator 136.

Figure 4:
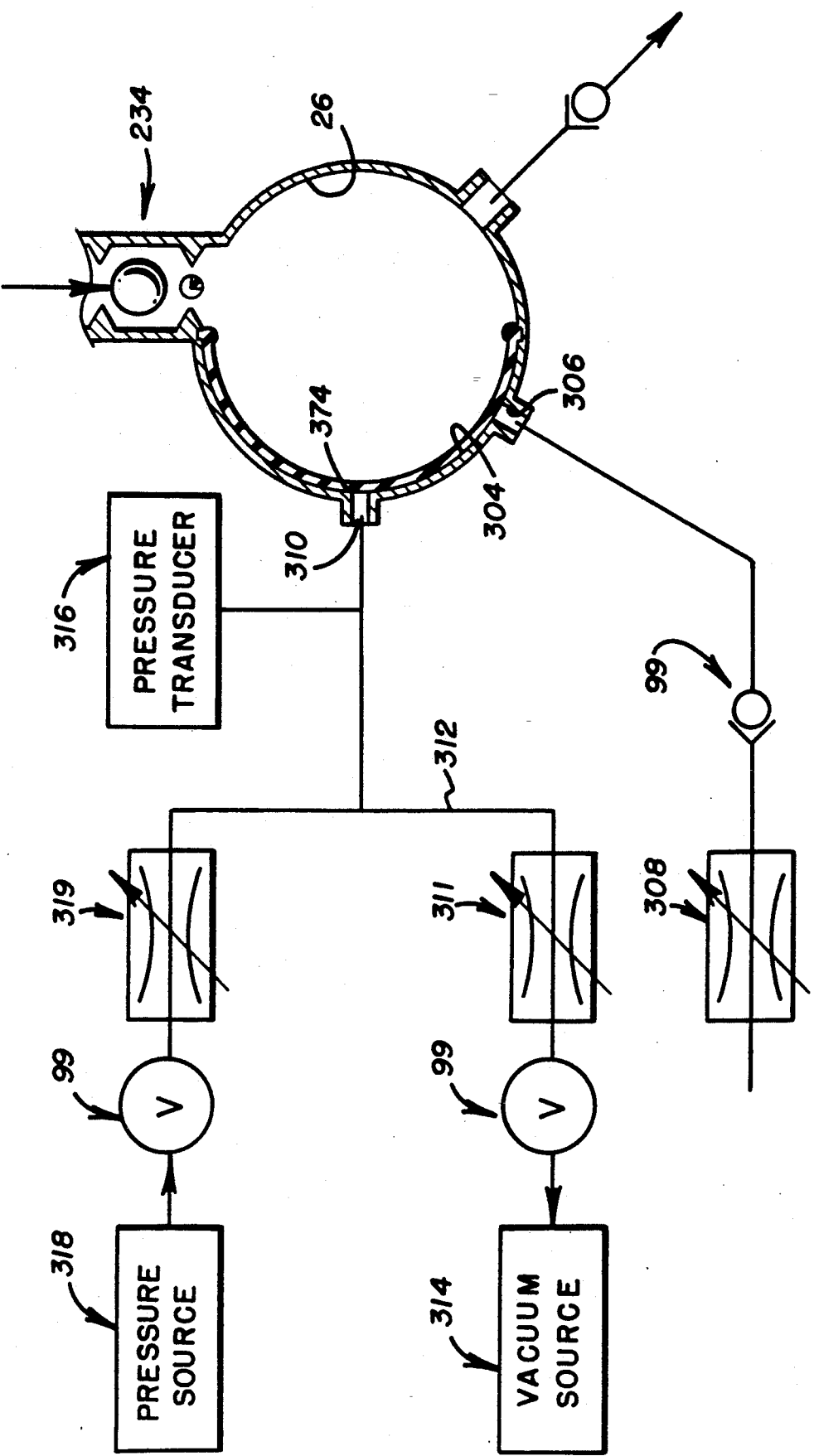
FIG. 4 illustrates, schematically, an alternate embodiment of a portion of an apparatus in accordance with the present invention.

FIG. 4 illustrates an alternate method for sensing when the pumping subchamber 26 is full. In the embodiment of FIG. 4 any one-way valve may be used as the check valve 234, that is, it is not necessarily a float valve. The pressurization subchamber 304 has an opening 306 which communicates with the atmosphere, for example via an orifice 308 which limits flow. When the diaphragm 374 blocks the entry 310, 306 or both, air cannot flow inwardly through the opening 306 into the pressurization subchamber 304 and from thence into a tube 312 communicating a vacuum source 314 with the entry 310 via flow control valve or orifice 311. As a result, the pressure in the tube 312 drops towards that generated by the vacuum source 314. A pressure transducer 316 measures pressure in the tube 312 and when it reaches a (low) pressure threshold this activates introduction of pressurized gas for a preselected period of time from a pressurized gas source 318 via an orifice 319 into the pressurization subchamber 304. The orifice 308 limits outward flow sufficiently so that the diaphragm can eject all of the blood from the pumping subchamber 26 or a one-way valve 99 can be used to prevent gas flow out of opening 306 when 304 is pressurized.

Figure 5:
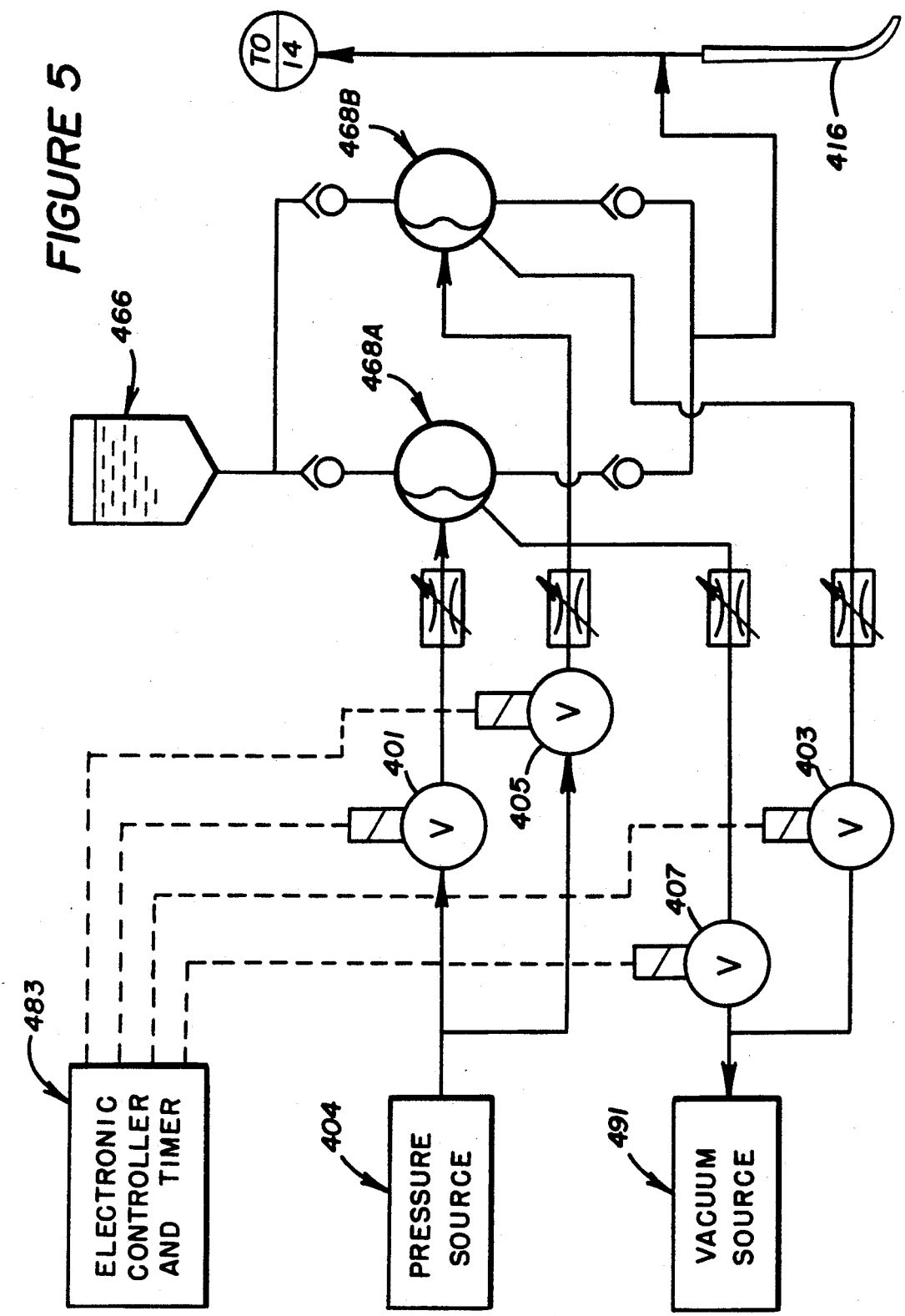
FIG. 5 illustrates, schematically, another alternate embodiment of a portion of an apparatus in accordance with the present invention.

When blood is being sucked by the suction wand 16 it is desired to mix this flow of blood with a continuous flow of anti-coagulant in the desired ratio of anti-coagulant to blood. An embodiment of the present invention as shown in FIG. 5 can be used to accomplished this. Two gas-actuated diaphragm pumps 468A,468B are used to pump anti-coagulant. These pumps alternate anti-coagulant ejection to provide constant or near-constant flow. The filling and ejection times for these pumps, from anti-coagulant source 466, are then necessarily about equal. The total duration of two pump ejections substantially equals the complete cycle time (ejection plus filling) of a batch by the main pump (not shown in FIG. 5). The initiation of anti-coagulant pump ejection occurs when the main pump ejects. Whenever the main pump ejects, each of the anti-coagulant pumps 468A,468B eject a single time each, one after the other. Then, when blood is pumped the anti-coagulant pumps 468A,468B produce continuous anti-coagulant flow. Pumping of the anti-coagulant pump 468A is initiated simultaneously with initiation of blood pumping by the main pump. This is accomplished under the control of electronic controller and timer 483. Initially solenoid valves 403 and 407 are open and 401 and 405 are closed. When the main pump starts its stroke valve 407 closes and valve 401 opens. When anti-coagulant pump 468A is emptied, at time, $t_1$, then electronic controller and timer 483 closes valve 401, opens valve 407, closes valve 403 and opens valve 405. At time, $t_2$, when pump 468B is emptied, the valves revert back to their initial condition. At the time $t_2$, the main pump has completed a full stroking cycle (has delivered a batch of blood and been refilled) and if full is ready to stroke again. Total blood pumping flow rate by the main pump (the average of the amount pumped during stroking and zero flow during filling) is approximately equal to the blood suction rate at the suction wand 416 as fixed by wand design and vacuum level. This can work better than adding the accumulator 173 of FIG. 2 in providing a constant ratio of anti-coagulant to blood during blood pumping.

In accordance with an autotransfusion method of the present invention a mixture of healthy blood cells, platelets, fluid, particulate matter and entrapped gases is recovered from a patient. The mixture is defoamed to remove the entrapped gases and is filtered to remove at least a portion of the particulate matter. The resulting filtered mixture enters the pumping chamber 26 of the main pump 24 and, after the pumping chamber 26 is full, is pumped out of the main pumping chamber 26 under pressure. Flow is prevented from occurring from the pumping chamber 26 back into the filtration apparatus. Flow is allowed from the filtering apparatus to the pump inlet port whenever the filtered mixture is not being pumped out of the pump outlet port 30. The filtered mixture is pumped through a narrow passage 50,150 in the tangential flow separator 36,136 or 236, either between a pair of membranes 38,40, or along the membrane 140, as the case may be, the passage 50,150 being no more than about 500 microns in height. The filtered mixture from the pumping chamber 26 or 126 is delivered to the passage 50,150 at a pressure in the passage 50,150 sufficient to expel blood fluid and small debris through the membrane 40 or 140 and at a flow rate through the passage 50,150 sufficient to prevent the blood cells from blocking or passing through the porous membrane 40 or 140.

In the case when the separator 36 is used, washing fluid is flowed across the narrow flow through passage 50. Blood fluid and washing fluid are removed from the outfacing surface of the second membrane 40. Pressure differentials are maintained across the membranes of the magnitudes previously set forth. In the case when separator 136 is used alone or in conjunction with one or more additional separators 236, washing fluid is either not added or is mixed with blood fluid before, within or after separator 136 or at any combination of these locations.

Industrial Applicability

The present invention provides a blood pumping and processing system 10 which has embodiments which can be used for intraoperative autotransfusion, plasmapheresis, hemodialysis, hemoconcentration and other therapeutic and/or diagnostic blood treatment applications. This system can provide blood filtration, plasma separation, metered anti-coagulant delivery and metered washing fluid delivery for plasma removal and replacement.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A blood filtering, pumping and tangential flow separating apparatus, comprising:
   a filter connected to receive a mixture of blood cells, platelets, blood fluid and particulate matter from a patient and being capable of removing at least a portion of said particulate matter larger than blood cells to form a filtered mixture, said filter having an outlet port from which said filtered mixture exits;
   a main pump having a pumping chamber having a pump inlet port arranged to receive said filtered mixture and a pump outlet port from which said filtered mixture is pumped;
   valve means between said filter outlet port and said pump inlet port for (1) preventing flow from said pumping chamber back into said filter and (2) allowing flow from said filter outlet port to said pump inlet port when said filtered mixture is not being pumped out of said pump outlet port;
   a tangential flow separator having a narrow passage having a porous membrane having an infacing and an outfacing surface and extending along said passage, said passage being no more than about 500 microns across, said passage extending from a separator inlet to a separator outlet;
   delivery means for delivering said filtered mixture from said pumping chamber to said separator inlet to provide a pressure in said passage sufficient to impel blood fluid through said porous membrane and a flow rate through said passage sufficient to prevent said blood cells at platelets from blocking or passing through said porous membrane;
   fluid removal means for removing blood fluid from said outfacing surface of said membrane, a pressure adjacent said outfacing surface of said membrane being less than the pressure in said passage; and
   means for returning the blood cells and platelets from said separator outlet to the patient.

2. An apparatus as set forth in claim 1, further including:
   a defoamer having an inlet port for receiving a recovered mixture of said blood cells, platelets, blood fluid, particulate matter and entrapped gases, said defoamer being adapted to remove at least a portion of said entrapped gases from said mixture, said defoamer being connected to deliver said mixture to said filter.

3. An apparatus as set forth in claim 2, wherein said main pump is a main diaphragm pump.

4. An apparatus as set forth in claim 3, wherein said main diaphragm pump pumping chamber is a substantially bi-concave chamber divided by a diaphragm into said pumping chamber and a pressurization subchamber, said diaphragm being movable to define said pumping chamber as substantially equal to the internal volume of said bi-concave chamber; and further including:
   means for pressurizing said pressurization subchamber sufficiently to impel said filtered mixture out of said pump outlet port.

5. An apparatus as set forth in claim 2, further including:
   an anti-coagulant pump positioned to deliver anti-coagulant to said recovered mixture prior to its introduction to said defoamer.

6. An apparatus as set forth in claim 5, further including:
   means for respectively starting and stopping said anti-coagulant pump in response to starting and stopping of pumping of said main pump.

7. An apparatus as set forth in claim 6, wherein said anti-coagulant pump is an anti-coagulant diaphragm pump.

8. An apparatus as set forth in claim 7, further including:
   washing fluid delivery means for delivering washing fluid to said passage.

9. An apparatus as set forth in claim 8, wherein said washing fluid delivery means is a washing fluid pump.

10. An apparatus as set forth in claim 9, further including:
    means for respectively starting and stopping said washing fluid pump in response to starting and stopping of pumping by said main pump.

11. An apparatus as set forth in claim 10, wherein said washing fluid pump is a washing fluid diaphragm pump.

12. An apparatus as set forth in claim 1, further including:
    washing fluid delivery means for delivering washing fluid to said passage.

13. An apparatus as set forth in claim 12, wherein said washing fluid delivery means is a washing fluid pump.

14. An apparatus as set forth in claim 13, further including:
    means for respectively starting and stopping said washing fluid pump in response to starting and stopping of pumping by said main pump.

15. An apparatus as set forth in claim 14, wherein said washing fluid pump is a washing fluid diaphragm pump.

16. An apparatus as set forth in claim 15, wherein said main pump is a main diaphragm pump.

17. An apparatus as set forth in claim 16, wherein said fluid removal means comprises a waste 18. An apparatus as set forth in claim 17, further including
the main pump and the waste pumps each having a fill period and a pumping period;
means for controlling the pumping period of said main pump to be longer than its fill period; and
means for controlling the waste pump to have a fill period corresponding to the main pump pumping period and to have a pumping period corresponding to the main pump fill period.

19. An apparatus as set forth in claim 18, wherein said washing fluid pump and said waste pump pumping volumes are coordinatedly selected to provide a given percent output hematocrit from the separator when the input hematocrit to the main pump is a selected value less than said given percent.

20. An apparatus as set forth in claim 19, wherein said given percent falls within a range from about 40% to about 60% and said selected value falls within a range from about 5% to about 40%.

21. An apparatus as set forth in claim 19, wherein said waste fluid pump pumping volume is fixed and said washing fluid pumping volume is varied to provide the given percent output hematocrit from the separator.

22. An apparatus as set forth in claim 1, wherein the pressure in said narrow passage of the tangential membrane exceeds the pressure adjacent the outfacing surface of the membrane by from about 25 mm Hg to about 150 mm Hg.

23. An apparatus as set forth in claim 1, wherein said valve means is a float valve.

24. An apparatus as set forth in claim 1, further including:
blood collecting means for collecting blood from adjacent a patient and delivering said blood to said inlet port.

25. An apparatus as set forth in claim 24, wherein:
said defoamer and said filter are combined in a single defoaming and filtering unit;
said unit includes an upper chamber having an upper non-liquid filled region; and
wherein said blood collecting means includes a conduit for delivering said recovered mixture to said defoamer and vacuum means for partially evacuating said upper region such that the pressure therein is lower than that of the surrounding atmosphere.

26. An apparatus as set forth in claim 1, further including:
an anti-coagulant pump positioned to deliver anti-coagulant to said blood prior to its introduction to said filter.

27. An apparatus as set forth in claim 26, further including:
means for respectively starting and stopping said anti-coagulant pump in response to starting and stopping of pumping of said main pump.

28. An apparatus as set forth in claim 27, wherein said anti-coagulant pump is an anti-coagulant diaphragm pump.

29. An apparatus as set forth in claim 28, further including:
washing fluid delivery means for delivering washing fluid to said passage.

30. An apparatus as set forth in claim 29, wherein said washing fluid delivery means is a washing fluid pump.

31. An apparatus as set forth in claim 30, further including:
means for respectively starting and stopping said washing fluid pump in response to starting and stopping of pumping by said main pump.

32. An apparatus as set forth in claim 31, wherein said washing fluid pump is a washing fluid diaphragm pump.

33. An apparatus as set forth in claim 26, further including:
anti-coagulant pump accumulator means for accumulating a portion of the anti-coagulant exiting said anti-coagulant pump; and
anti-coagulant metering means for metering said portion of said anti-coagulant to said recovered mixture when said anti-coagulant pump is not delivering anti-coagulant to said recovered mixture.

34. An apparatus as set forth in claim 1, wherein said tangential flow separator includes an additional aqueous solution permeable membrane having an infacing surface and an outfacing surface and extending along said passage; and further including:
washing fluid delivery means for delivering washing fluid against the outfacing surface of said additional membrane at a pressure sufficiently high whereby said washing fluid passes therethrough and into said passage.

35. An apparatus as set forth in claim 34, wherein said washing fluid delivery means is a washing fluid pump.

36. An apparatus as set forth in claim 35, further including:
means for respectively starting and stopping said washing fluid pump in response to starting and stopping of pumping by said main pump.

37. An apparatus as set forth in claim 1, further including:
main pump accumulator means for accumulating a portion of the filtered mixture exiting said pump outlet port; and
filtered mixture metering means for metering said portion of said filtered mixture to said passage when said main pump is not pumping said filtered mixture out of said pump outlet port.

38. An apparatus as set forth in claim 37, further including:
an anti-coagulant pump positioned to deliver anti-coagulant to said recovered mixture prior to its introduction to said defoamer.

39. An apparatus as set forth in claim 38, further including:
anti-coagulant pump accumulator means for accumulating a portion of the anti-coagulant exiting said anti-coagulant pump; and
anti-coagulant metering means for metering said portion of said anti-coagulant to said recovered mixture when said anti-coagulant pump is not delivering anti-coagulant to said recovered mixture.

40. An apparatus as set forth in claim 39, further including:
washing fluid delivery means for delivering washing fluid to said passage.

41. An apparatus as set forth in claim 40, further including:
washing fluid accumulator means for accumulating a portion of the washing fluid from said washing fluid delivery means; and washing fluid metering means for metering said portion of said washing fluid to said passage when said washing fluid delivery means is not delivering washing fluid to said passage.

42. An apparatus as set forth in claim 37, further including:
washing fluid delivery means for delivering washing fluid to said passage.

43. An apparatus as set forth in claim 42, further including:
washing fluid accumulator means for accumulating a portion of the washing fluid from said washing fluid delivery means; and
washing fluid metering means for metering said portion of said washing fluid to said passage when said washing fluid delivery means is not delivering washing fluid to said passage.

44. An apparatus as set forth in claim 1, further including:
washing fluid delivery means for delivering washing fluid to said passage.

45. An apparatus as set forth in claim 44, further including:
washing fluid accumulator means for accumulating a portion of the washing fluid from said washing fluid delivery means; and
washing fluid metering means for metering said portion of said washing fluid to said passage when said washing fluid delivery means is not delivering washing fluid to said passage.

46. An apparatus as set forth in claim 1, further including:
bypass means for bypassing said filtered mixture exiting said pump outlet port around said tangential flow separator in response to the flow rate from said pump outlet port exceeding the flow through capacity of said tangential flow separator.

47. An apparatus as set forth in claim 1, further including:
oscillation generating means for generating oscillations in said passage.

48. A blood pumping and fluid introduction apparatus, comprising:
a main pump having a pumping subchamber having a pump inlet port arranged to receive blood and a pump outlet port from which said blood is pumped, said main pump having a substantially biconoave main pump chamber divided by a main pump diaphragm into said pumping subchamber and a pressurization subchamber;
a blood delivery system for delivering blood to said pump inlet port;
valve means between said blood delivery system and said pump inlet port for (1) preventing flow from said pumping subchamber back into said blood delivery system and for (2) allowing flow from said blood delivery system to said pump inlet port when blood is not being pumped out of said pump outlet port;
means for determining when said main pump pumping subchamber is substantially full;
main pump pressurizing means for pressurizing said main pump pressurization subchamber, in response to said main pump pumping subchamber being substantially full, sufficiently to impel substantially all of said blood out of said pump outlet port;
a fluid introduction pump positioned to deliver a fluid to said blood; and
means for respectively starting and stopping said fluid introduction pump in response respectively to starting and stopping of pumping of said main pump.

49. An apparatus as set forth in claim 48, wherein said blood is a portion of a recovered mixture which includes healthy blood cells, platelets, plasma and particulate matter, and wherein said blood delivery system includes a filter connected to receive said recovered mixture and being capable of removing at least a portion of said particulate matter to form a filtered mixture, said filter having an outlet port from which said filtered mixture exits.

50. An apparatus as set forth in claim 49, wherein said blood delivery system further includes a defoamer having an inlet port for receiving said recovered mixture and being capable of removing at least a portion of any entrapped gases therefrom and delivering a resulting defoamed mixture to said filter.

51. An apparatus as set forth in claim 50, wherein said blood delivery system further includes blood and particulate matter collecting means for collecting blood and particulate matter from adjacent a patient and delivering said blood and particulate matter to said inlet port.

52. An apparatus as set forth in claim 51, wherein:
said defoamer and said filter are combined in a single defoaming and filtering unit;
said unit includes an upper chamber having an upper non-liquid filled region; and
wherein said blood and particulate matter collecting means includes a conduit for delivering said recovered mixture to said defoamer and vacuum means for partially evacuating said upper region such that the pressure therein is lower than that of the surrounding atmosphere.

53. An apparatus as set forth in claim 48, wherein said fluid pump has a substantially biconcave chamber divided by a diaphragm into a fluid pump pumping subchamber and a fluid pump pressurization subchamber and wherein said main pump pressurizing means, simultaneously with pressurizing said bi-concave main pump pressurization subchamber, also pressurizes said fluid pump pressurization subchamber sufficiently to substantially empty said fluid from said fluid pump pumping subchamber.

54. An apparatus as set forth in claim 53, wherein said fluid delivered by said fluid introduction pump comprises anti-coagulant.

55. A blood pumping and processing apparatus comprising:
a rigid main pump housing having an internal wall structure defining a bi-conoave chamber;
a main pump diaphragm sealed at its periphery to said internal wall structure, said main pump diaphragm dividing said chamber into a pressurization subchamber and a stroking subchamber, said diaphragm being of a shape and size sufficient to fit substantially matingly against said internal wall structure defining either of said subchambers and being formulated of a material which is sufficiently flexible to allow said diaphragm to fit substantially matingly against said internal wall structure defining each of said subchambers whereby by diaphragm motion and flexing each of said subchambers can vary in size from substantially zero volume to substantially the volume of said chamber;

inlet valve means for delivering blood to said stroking subchamber and for preventing backflow therethrough;

outlet valve means for permitting blood to leave said stroking subchamber and for preventing flow back into the stroking subchamber;

means for pressurizing said pressurization subchamber at a controlled rate sufficiently to motivate said diaphragm to substantially matingly fit against said internal wall structure defining said stroking subchamber to expel substantially all blood in said stroking subchamber through said outlet valve means;

means for depressurizing said pressurization subchamber at a controlled rate sufficiently to motivate said diaphragm to substantially matingly fit against said internal wall structure defining said pressurization subchamber;

means for sensing when said stroking subchamber is substantially full and for activating said pressurizing means when said stroking subchamber is substantially full; and means for processing blood flowing to or from said main pump.

56. An apparatus as set forth in claim 55, wherein said means for sensing when said stroking subchamber is substantially full includes means for detecting the change in pressure in said pressurization subchamber as a pressurizing gas is added thereto.

57. An apparatus as set forth in claim 56, wherein said inlet valve means comprises a float valve having a float having a specific gravity between about 0.8 and 1.0.

58. An apparatus as set forth in claim 55, further including:
means for periodically activating said pressurization means;
means for detecting the rate of increase in pressure in said pressurization subchamber on activating of said periodic activating means; and
means for aborting operation of said pressurizing means if said rate of increase in pressure in said pressurization subchamber is less than a selected value representative of said float valve being closed.

59. An apparatus as set forth in claim 55, wherein said blood processing means removes or modifies a component of the blood.

60. An apparatus as set forth in claim 55, wherein said blood processing means removes components larger than red cells from said blood.

61. An apparatus as set forth in claim 60, wherein said blood processing means comprises a tangential flow separator for removing components smaller than red cells and platelets via a porous membrane.

62. An apparatus as set forth in claim 55, wherein said blood processing means comprises a tangential flow separator for removing components smaller than red cells and platelets via a porous membrane.

63. A method of separating blood cells from blood plasma, comprising:
filtering and defoaming a recovered mixture of healthy blood cells, platelets, plasma, particulate matter and entrapped gases to remove at least a portion of said particulate matter therefrom and at least a portion of the entrapped gases to form a defoamed and filtered mixture;
pumping said defoamed and filtered mixture into an inlet of a tangential flow separator having a narrow flow through passage having a porous membrane having an infacing surface and an outfacing surface and extending along the passage, the passage being no more than about 500 microns across, said passage extending from said separator inlet to a separator outlet, said pumping providing a pressure within said passage sufficient to impel plasma through the porous membrane and a flow rate through the passage sufficient to prevent the blood cells from blocking or passing through the porous membrane; and
removing plasma from the outfacing surface of the membrane by maintaining a pressure adjacent said outfacing surface of said membrane as less than that in the passage.

64. A method as set forth in claim 63, further including:
delivering washing fluid to said passage.

65. A method as set forth in claim 64, further including starting and stopping delivery of said washing fluid substantially simultaneously with starting and stopping of pumping of said defoamed and filtered mixture.

66. A method as set forth in claim 65, further including:
delivering anti-coagulant to said recovered mixture prior to its defoaming.

67. A method as set forth in claim 66, further including:
starting and stopping delivery of said anti-coagulant substantially simultaneously with starting and stopping of pumping of said defoamed and filtered mixture.

68. A method as set forth in claim 63, further including:
delivering anti-coagulant to said recovered mixture prior to its defoaming.

69. A method as set forth in claim 68, further including:
starting and stopping delivery of said anti-coagulant substantially simultaneously with starting and stopping of pumping of said defoamed and filtered mixture.

70. A method as set forth in claim 63, wherein said tangential flow separator includes an additional membrane having an infacing surface and an outfacing surface and extending along the passage, and further including:
delivering washing fluid against the outfacing surface of said additional membrane at a pressure sufficiently high whereby said washing fluid passes therethrough and into said passage.

71. A method as set forth in claim 70, further including starting and stopping delivery of said washing fluid substantially simultaneously with starting and stopping of pumping of said defoamed and filtered mixture.

72. A method as set forth in claim 71, further including:
delivering anti-coagulant to said recovered mixture prior to its defoaming.

73. A method as set forth in claim 72, further including:
starting and stopping delivery of said anti-coagulant substantially simultaneously with starting and stopping of pumping of said defoamed and filtered mixture.

74. A blood pumping and treating apparatus, comprising:

a main pump having a pumping subchamber having a pump inlet port arranged to receive blood and a pump outlet port from which said blood is pumped;

a blood delivery system for delivering blood to said pump inlet port;

valve means between said blood delivery system and said pump inlet port for (1) preventing flow from said pumping subchamber back into said blood delivery system and for (2) allowing flow from said blood delivery system to said pump inlet port when blood is not being pumped out of said pump outlet port;

means for determining when said main pump pumping subchamber is substantially full;

means for activating said pump to pump blood out of said main pump pumping subchamber in response to said main pump pumping subchamber being substantially full sufficiently to impel substantially all of said blood out of said pump outlet port;

a wash fluid pump positioned to deliver wash fluid to said blood;

means for determining inlet blood hematocrit to said main pump pumping subchamber; and means for controlling delivery of fluid by said wash fluid pump as a function of inlet blood hematocrit to be in an amount to provide output blood hematocrit following introduction of said wash fluid which falls within a selected range.

75. An apparatus as set forth in claim 74, further including:

means for delivering the outlet blood to a patient.

76. An apparatus as set forth in claim 74, further including:

a tangential flow separator having a narrow passage having a porous membrane having an infacing and an outfacing surface and extending along said passage, said passage being no more than about 500 microns across, said passage extending from a separator inlet to a separator outlet;

delivery means for delivering said filtered mixture from said pumping subchamber to said separator inlet to provide a pressure in said passage sufficient to impel blood fluid through said porous membrane and a flow rate through said passage sufficient to prevent said blood cells and platelets from blocking or passing through said porous membrane;

fluid removal means for removing blood fluid from said outfaoing surface of said membrane, a pressure adjacent said outfacing surface of said second membrane being less than the pressure in said passage; and means for delivering the blood cells and platelets from said separator outlet to a patient.

77. An apparatus as set forth in claim 76, wherein said fluid removal means comprises a waste pump, and wherein said main pump and said waste pump each are diaphragm pumps and each having a fill period and a pumping period; and further including:

means for controlling the pumping period of said main pump to be longer than its fullperiod; and means for controlling the waste pump to have a fill period corresponding to the main pump pumping period and to have a pumping period corresponding to the main pump fill period.

78. An apparatus as set forth in claim 77, wherein said washing fluid pump and said waste pump pumping volumes are coordinatedly selected to provide a given percent output hematocrit from the separator when the input hematocrit to the main pump is a selected value less than said given percent.

79. An apparatus as set forth in claim 78, wherein said given percent falls within a range from about 40% to about 60% and said selected value falls within a range from about 5% to about 40%.

80. An apparatus as set forth in claim 17 wherein the waste pump is a waste diaphragm pump.

* * * * *